(12) United States Patent
Rensch et al.

(10) Patent No.: US 9,192,934 B2
(45) Date of Patent: Nov. 24, 2015

(54) INSERT ASSEMBLY FOR A MICROFLUIDIC DEVICE

(71) Applicant: General Electric Company, Schenectady, NY (US)

(72) Inventors: Christian Friedrich Peter Rensch, Munich (DE); Victor Donald Samper, Kircheeon (DE); Christoph Boeld, Munich (DE); Ruben Julian Horvath-Klein, Munich (DE)

(73) Assignee: General Electric Company, Niskayuna, NY (US)

( * ) Notice: Subject to any disclaimer, the term of this patent is extended or adjusted under 35 U.S.C. 154(b) by 110 days.

(21) Appl. No.: 13/731,347

(22) Filed: Dec. 31, 2012

(65) Prior Publication Data

US 2014/0120010 A1 May 1, 2014

Related U.S. Application Data

(60) Provisional application No. 61/718,434, filed on Oct. 25, 2012.

(51) Int. Cl.

| | |
|---|---|
| *B01L 3/00* | (2006.01) |
| *B32B 37/00* | (2006.01) |
| *B32B 37/14* | (2006.01) |
| *G01N 1/00* | (2006.01) |
| *G01N 27/447* | (2006.01) |
| *G01N 30/60* | (2006.01) |

(52) U.S. Cl.
CPC ..... *B01L 3/502707* (2013.01); *B01L 3/502715* (2013.01); *B01L 2200/027* (2013.01); *B01L 2200/0631* (2013.01); *B01L 2300/0681* (2013.01); *B01L 2300/0816* (2013.01); *B01L 2300/0887* (2013.01); *B01L 2300/12* (2013.01); *G01N 27/44791* (2013.01); *G01N 30/6095* (2013.01); *Y10T 29/49826* (2015.01); *Y10T 156/10* (2015.01)

(58) Field of Classification Search
None
See application file for complete search history.

(56) References Cited

U.S. PATENT DOCUMENTS

| | | | |
|---|---|---|---|
| 6,969,850 | B2 | 11/2005 | Staats |
| 7,605,002 | B2 | 10/2009 | Summersgill et al. |
| 7,618,576 | B2 | 11/2009 | Staats |
| 7,641,861 | B2 | 1/2010 | Kimizuka |
| 8,011,082 | B2 | 9/2011 | Weekamp et al. |
| 8,153,085 | B2 | 4/2012 | Hwang et al. |
| 2002/0164816 | A1 | 11/2002 | Quake |
| 2005/0000900 | A1 | 1/2005 | Huang et al. |

(Continued)

OTHER PUBLICATIONS

Search Report and Written Opinion from PCT Application No. PCT/US2013/066792 dated Mar. 3, 2014.

(Continued)

*Primary Examiner* — Lyle Alexander
*Assistant Examiner* — Jennifer Wecker
(74) *Attorney, Agent, or Firm* — Robert M. McCarthy

(57) ABSTRACT

Techniques and devices are provided related to insert assemblies that may be used in conjunction with microfluidic devices. In one embodiment, the insert assemblies include a functional material, such as a solid stationary phase, that may be coupled to a microfluidic pathway via the insert assembly. In this manner, solid stationary phase materials that may be challenging to directly apply to a microfluidic device may be separately enclosed inside the insert element prior to assembly into a microfluidic device, such as a microfluidic chip.

6 Claims, 12 Drawing Sheets

(56) References Cited

U.S. PATENT DOCUMENTS

| | | | |
|---|---|---|---|
| 2007/0128652 A1* | 6/2007 | Woudenberg et al. | 435/6 |
| 2007/0138076 A1 | 6/2007 | Daridon et al. | |
| 2008/0190840 A1 | 8/2008 | Eickhoff et al. | |
| 2009/0215194 A1* | 8/2009 | Magni et al. | 436/174 |
| 2010/0048867 A1 | 2/2010 | Mueller | |
| 2010/0303687 A1* | 12/2010 | Blaga et al. | 422/504 |
| 2011/0070160 A1 | 3/2011 | Nutt et al. | |
| 2011/0186165 A1* | 8/2011 | Borenstein et al. | 137/833 |
| 2012/0115189 A1* | 5/2012 | Jovanovich et al. | 435/91.2 |

OTHER PUBLICATIONS

Wessmann et al., "Cryptate mediated nucleophilic 18F-fluorination without azeotropic drying" Nuklearmedizin 2012 vol. 51 Issue 1 pp. 1-31.

Yin, Hongfeng, et al., "Microfluidic Chip for Peptide Analysis with an Integrated HPLC Column, Sample Enrichment Column, and Nanoelectrospray Tip", Analytical Chemistry, ACS Publications, pp. 527-533, vol. 77, Issue 2, Dec. 9, 2005.

"Topas® 60155-04", Topas Advanced Polymers, Jan. 19, 2006.

"Topas® 60175-04", Topas Advanced Polymers, May 30, 2006.

Wessmann et al., "Preparation of highly reactive [18F]fluoride without any evaporation step", The Journal of Nuclear Medicine, pp. 1-2, vol. 52, 2011.

Leonardis et al., "On-chip pre-concentration and complexation of [18F]fluoride ions via regenerable anion exchange particles for radiochemical synthesis of Positron Emission Tomography tracers", Journal of Chromatography A, Elsevier, pp. 4714-4719, vol. 1218, Issue 29, Jul. 22, 2011.

Lebedev et al., Batch-reactor microfluidic device: first human use of a microfluidically produced PET radiotracer, Lab on a Chip, D01:10.1039/c21c40853h 2012.

* cited by examiner

INSERT ASSEMBLY FOR A MICROFLUIDIC DEVICE

CROSS-REFERENCE TO RELATED APPLICATIONS

This application claims priority to U.S. Provisional Patent Application No. 61/718,434, entitled "Method for Microfluidic On-Chip Resin Integration," filed Oct. 25, 2012, which is herein incorporated in its entirety by reference for all purposes.

BACKGROUND

Multiple processes in chemistry employ a solid stationary phase for purification, filtering or separation of reagents or reagent mixtures. Conventional implementations may include columns packed with a resin containing beads or porous media of a certain size, with a functionalized surface, and/or specific material properties. Solid stationary phases are often implemented in chromatography. For example, solid stationary phases may be used in partition, normal-phase, displacement, reversed-phase, size-exclusion, ion-exchange and bioaffinity chromatography. Other implementations are solid phase extraction (SPE) and ion exchange columns as they are used e.g. in radiochemistry for purification and concentration of radioactive species.

Microfluidic technology has applications in chemistry, biochemistry, biology, physics and pharmaceutics. Microfluidic techniques typically involve small sample volumes, e.g., in the range of several nanoliters to hundreds of microliters, and offers advantages such as low reagent consumption, efficient thermal control, small system footprint at a high level of functionality integration and versatile, disposable microfluidic core components. Whereas microfluidic systems have developed over several decades, only a few microfluidics based products have succeeded and entered the market. Challenges in microfluidics may relate to system reliability, the micro-to macro interface, system control, readout, overall system complexity, manufacturing complexity and resulting cost of microfluidic consumable products, and the implementation of conventional chemical methods utilized during analysis, synthesis and purification of chemical compounds. With regard to the incorporation of chemical techniques into microfluidic environments, the implementation of stationary phases and beads onto microfluidic chip devices suitable for mass production is particularly challenging.

BRIEF DESCRIPTION

In one embodiment, a method of manufacturing a microfluidic device is provided. The method includes a step of providing a substrate with a microfluidic pathway and a passageway formed in the substrate that interrupts the microfluidic pathway. The method also includes a step of providing an insert assembly in the passageway configured to be disposed in-line with the microfluidic pathway and to bridge the microfluidic pathway across the passageway such that a sample material in the microfluidic pathway passes through the insert assembly. The method further includes providing a top layer disposed a first surface of the substrate and a bottom layer disposed on a second surface of the substrate opposing the first surface; and coupling the top layer and the bottom layer to the insert assembly.

In another embodiment a microfluidic chip is provided. The microfluidic chip includes: a substrate with a microfluidic pathway and a passageway formed in the substrate that interrupts the microfluidic pathway; an insert assembly in the passageway disposed in-line with the microfluidic pathway and bridging the microfluidic pathway across the passageway, wherein the insert assembly comprises a housing with a central bore and a functional material disposed in the bore; a top layer disposed a first surface of the substrate; and a bottom layer disposed on a second surface of the substrate opposing the first surface, wherein at least one of the substrate, the top layer, or the bottom layer is formed from a first material comprising different thermal properties relative to a second material forming the insert housing of the insert assembly such that first material and the second material have different softening or melting temperatures. In one embodiment, the insert and the substrate material can be manufactured from different materials or from the same material at different material grades resulting in a softening/deformation or melting temperature difference between the insert and the substrate material.

In another embodiment a method of manufacturing a microfluidic device is provided. The method includes a step of providing a substrate with a microfluidic pathway and a passageway formed in the substrate that interrupts the microfluidic pathway. The method also includes providing an insert assembly in the passageway configured to be disposed in-line with the microfluidic pathway, wherein the insert assembly comprises an insert housing defining a bore; providing a top layer disposed a first surface of the substrate and a bottom layer disposed on a second surface of the substrate opposing the first surface; enclosing the insert assembly between the top layer and the bottom layer, and within the passageway such that an enclosure formed around the insert assembly comprises a gap between the insert housing and one or more of the top layer, the bottom layer, and the passageway; and deforming the insert housing to fill the gap to couple the insert assembly to the top layer and the bottom layer. It should also be understood that certain embodiments of the disclosure may be implemented in which the substrate material deforms around an insert housing with a relatively higher deformation or melting temperature.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

The present disclosure relates to microfluidic devices that incorporate stationary phase components. In certain embodiments, the present disclosure provides a solid stationary phase implementation strategy for microfluidic chip-based systems that incorporate an insert and that are suitable for mass-production. The design and the materials used may be compatible with typical packaging techniques.

Figure 1:
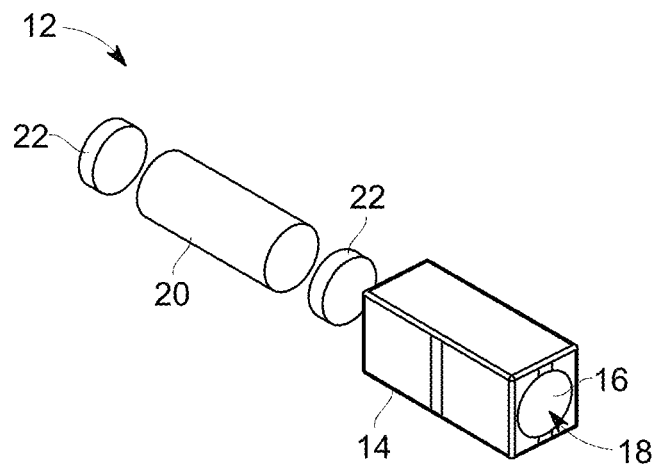
FIG. 1 is an exploded view of an insert assembly in accordance with aspects of the present disclosure.
Figure 2:
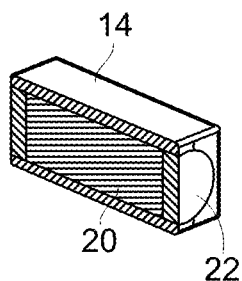
FIG. 2 is a cross-sectional view of the insert assembly of FIG. 1.
Figure 3:
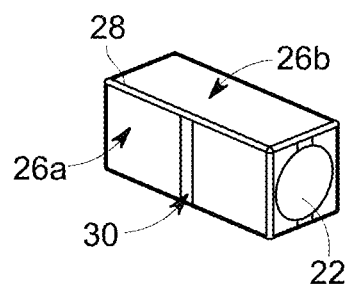
FIG. 3 is a perspective view of the insert assembly of FIG. 1.

Certain microfluidic techniques may implement conventional solid resin cartridges that, rather than being in-line as a functional element of the chip, are connected via tubing to the microfluidic device. Other techniques may incorporate bead technology, whereby the beads are placed within the chip. Further, liquid compounds may be introduced on to microfluidic devices and later cured to a solid or porous resin utilizing radiation, such as UV light or thermally induced curing. All of these implementations are labor intensive, often involve a change of functional materials compared to established conventional processes, may provide inconsistent results, and are difficult to automate for assembling of microfluidic systems on a mass-production scale. Provided herein are microfluidic devices that include integrated insert assemblies that are after assembly in-line with the fluid path on-chip and that may be prior to assembly formed and processed separately from the chip, which provides more manufacturing flexibility. For example, by using an insert assembly, the manufacturing conditions for the functional material in the insert assembly, e.g., a solid stationary phase, may be selected without regard for the components already in-place on the chip, which reduces the complexity of manufacturing and increases the flexibility of type and quantity of resins that can be implemented on-chip. The insert assemblies and the corresponding receptacles on the chip may also be standardized such that chips may be implemented to include a variety of stationary phases without additional processing steps for forming the insert assemblies and/or the insert fillings Turning to the figures, FIG. 1 is an exploded view of an insert assembly 12 according to certain embodiments of the present disclosure. The insert assembly 12 comprises an insert housing 14 that defines a bore or passageway 16 through the insert housing 14 having an opening 18 on opposing sides. In one embodiment, the passageway 16 may be filled with a reaction material or functional material (e.g., resin) 20. One or more porous caps 22 enclose the functional material 20 in the passageway 16. The passageway 16 may be any suitable shape, such as generally circular or round in cross-section (e.g., forming a circular opening 18) or rectangular or elliptical. The insert housing 14 includes exterior surfaces 26 that meet up at a junction 28 (e.g., exterior surfaces 26a and 26b). In one embodiment, the exterior surfaces 26 may form 90 degree angles at the junction 28, defining a generally rectangular cross-section for the insert housing 14, as shown in FIG. 2. That is, the insert housing 14 may be generally cuboid or a rectangular cuboid. In other embodiments, the insert housing 14 may assume other suitable shapes specifically formed to fit into corresponding recesses or receptacles on a microfluidic device and/or to support an optimized force and pressure distribution during compression or thermo-forming of the insert versus the surround substrate material during bonding. Further, in one embodiment, the insert housing 14 may form a generally rectangular exterior shape around a generally round passageway 16. FIG. 3 is a perspective view of an insert assembly 12 showing the porous caps 22 in the opening 18 positioned to close the passageway 16. The porous caps 22 may be formed from the same material as the insert housing 14 or may be formed from other materials, e.g., the seals may be frit elements. The exterior surface 26 may include additional features, such as ribs (e.g., rib 30), grooves, or mating features that facilitate alignment within a microfluidic chip.

Figure 4:
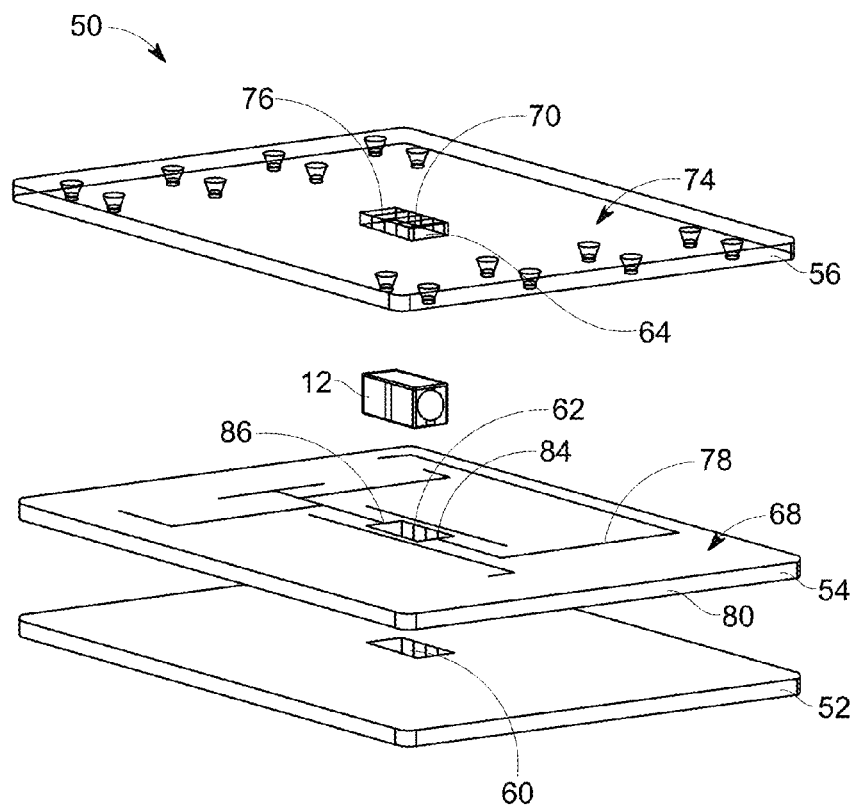
FIG. 4 is an exploded view of a microfluidic chip including an insert assembly in accordance with aspects of the present disclosure.

FIG. 4 is an exploded view of a microfluidic chip 50 including the insert assembly 12. The microfluidic chip includes a bottom layer 52, middle layer 54, and top layer 56. The insert assembly 12 is positioned within aligned passages disposed within the microfluidic chip 50 and on the bottom layer 52, middle layer 54, and top layer 56. For example, bottom layer 52 includes a bottom recess or passage 60 formed in the material of the bottom layer 52 that aligns with a middle passage 62 in the middle later 54 and a top recess or passage 64 formed in the top layer 56. In the case of the middle layer 54, the middle passage 62 may extend completely through the middle layer 54 so that the insert assembly 12 protrudes at least slightly from a top surface 68 and a bottom surface (not shown) of the middle layer 54 and so that the directly contacts the bottom layer 52, middle layer 54, and top layer 56. One or both of the top layer 56 or the bottom layer 52 may also include caps that cover and seal the insert assembly 12 within the microfluidic chip 50. For example, a cap 70 may be disposed on an exterior surface 74 of the top layer 56. In the depicted embodiment, the cap 70 may be clear so that the insert assembly 12 is visible to an operator. Further, the cap 70 may include one or more alignment features 76 that mate with complementary features (e.g., ribs 30) on the insert assembly 12. Such features may also help align the layers together during manufacturing. While the depicted embodiment shows a three-layer microfluidic chip 50, it should be understood that the insert assembly 12 as provided herein may be used in conjunction with a microfluidic chip 12 with one or more layers.

Figure 5:
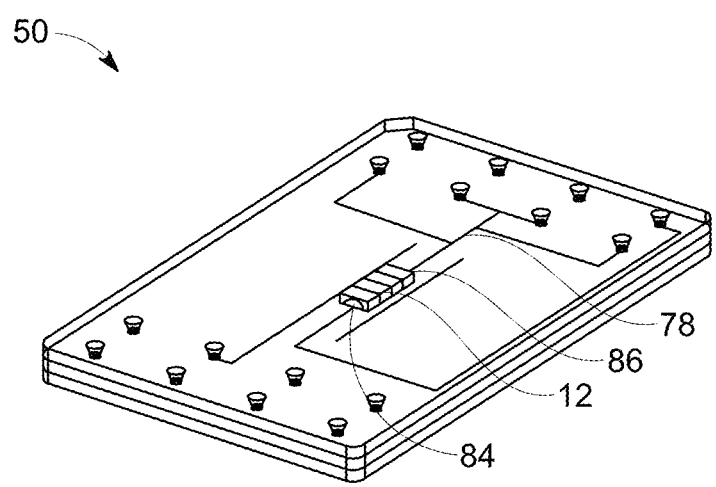
FIG. 5 is a perspective view of the microfluidic chip of FIG. 4.

In one embodiment, the middle layer 54 is formed from a substrate and includes functional components, such as fluidic pathways 78, formed in the substrate 80. As depicted, a portion of the fluidic pathway 78 comprises a first terminus 84 and a second terminus 86. That is, prior to assembly of the microfluidic chip 50, the fluidic pathway 78 is interrupted by the passageway 64, which extends through the substrate 80. FIG. 5 is a perspective view of an assembled chip including the insert assembly. The insert assembly 12 bridges the first terminus 84 and the second terminus 86 to complete the fluidic pathway 78 when inserted. In one embodiment, the bottom layer 52 and the top layer 56 may function to enclose the fluidic pathways 78 formed in the middle layer 54. Further, one or both of the bottom layer 52 and the top layer 56 may be transparent to allow viewing of the insert assembly 12 and the fluidic pathways 78.

Figure 6:
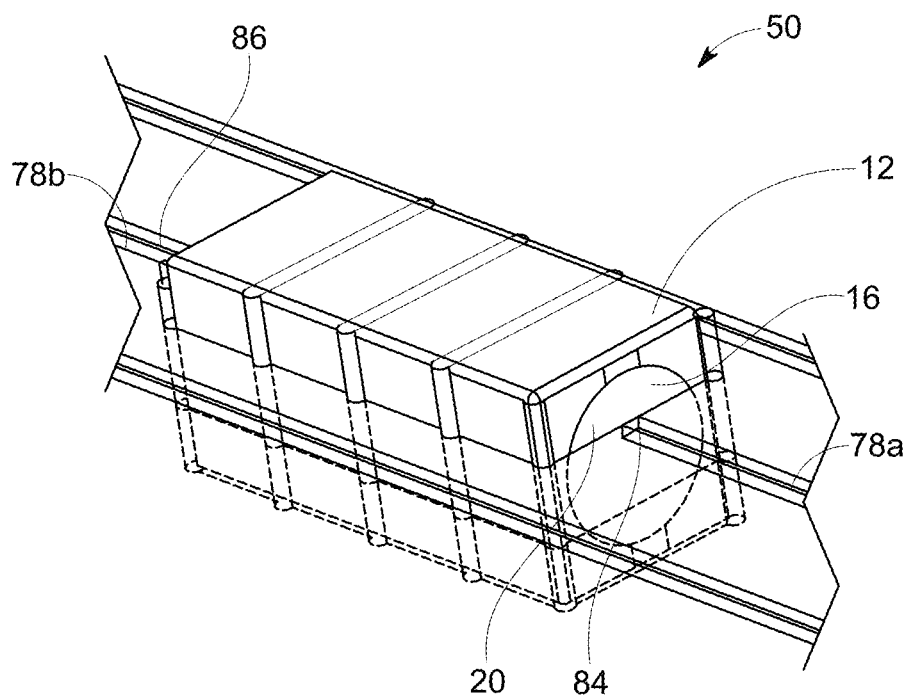
FIG. 6 is a detail view of the insert assembly positioned within the microfluidic chip of FIG. 4.

FIG. 6 is a detail view of the insert assembly 12 in position on the microfluidic chip 50. The fluidic pathway 78a is positioned so that the first terminus 84 is in-line with the passageway 16 of the insert assembly 12. In operation, the sample exits the fluidic pathway 78a through the first terminus 84, which is flush with, i.e., directly contacts, the insert assembly 12 and enters the passageway 16 to interact with the functional material 20. After contact with the functional material 20, the sample exits the insert assembly and renters the fluidic pathway 78b via the second terminus 86. Accordingly, the microfluidic chip 50 is assembled so that the insert assembly 12 is positioned in-line with the fluidic pathway 78. Such an arrangement avoids extraneous pathways, tubing, or connectors between the functional material 20 and the chip 50.

Figure 7:
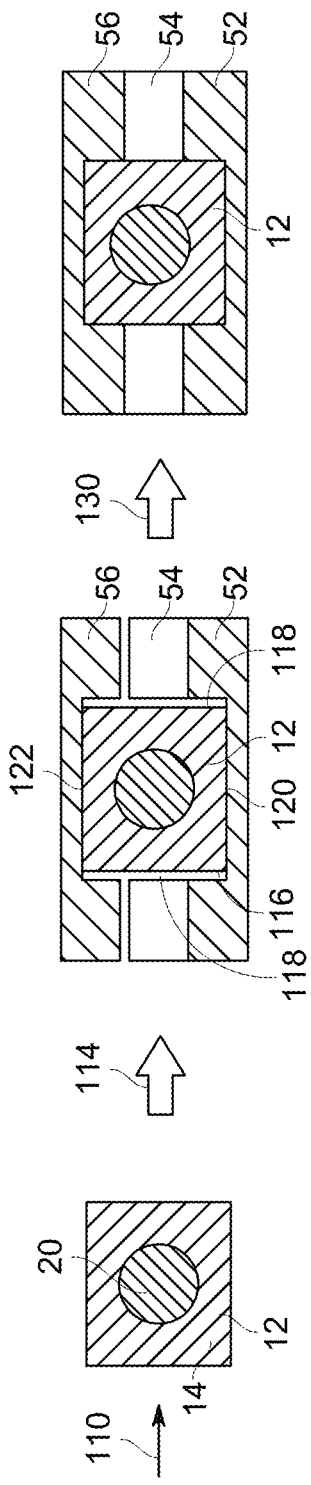
FIG. 7 is a schematic view of a process for forming (bonding) a microfluidic chip showing intermediate assemblies of the manufacturing process in cross-section including an insert assembly in accordance with aspects of the present disclosure.

FIG. 7 is a schematic process diagram of a method 100 of assembling a microfluidic chip 50 in accordance with embodiments of the present disclosure. Certain steps of the method 100 may be implemented manually or automatically. Further, certain steps of the method 100 may be controlled by, monitored by, or executed by a processor-based machine including a memory storing instructions for facilitating control systems for all or part of a particular step of the method 100. The memory may be any suitable volatile memory device and/or a non-volatile mass-storage device. The processor-based machine may be configured to perform the steps without user intervention or may be configured to receive a user input and execute instructions in response. Accordingly, such machines may include suitable user interface components, including a display and/or user input controls.

The method starts at step 110 with formation of the insert assembly 12. For example, in one embodiment, the insert housing 14 may be formed via a suitable process, such as casting, molding or machining. In one embodiment, the passageway 16 is formed within the insert housing 14 via casting, molding or machining. In other embodiments, the passageway 16 is formed by drilling through the insert housing 14. The insert housing 14 may be mass-produced in suitable sizes and shapes. Once formed, the open passageway 16 through the insert housing 14 is filled with the functional material 20. The functional material 20 may include any suitable functional component for a microfluidic device. For example, the functional material 20 may include solid stationary phase components for phase extraction, such as reverse phase extraction, ion exchange extraction, etc. The functional material 20 may be formed from solids, e.g., particles or beads, gels, and/or liquids and may be provided wet or dry within the insert housing 14. In certain embodiments, one or more caps (e.g., porous caps 22, see FIG. 1) are positioned to hold the functional material 20 within the insert assembly. In one embodiment, the insert assembly 12 may include multiple functional materials 20, e.g., lined up in a row within the insert housing 14.

At step 114, the insert assembly 12 is selected to be placed into a recess 116. In certain embodiments, the insert assembly 12 may be selected from a library of insert assemblies 12, each having a different size, shape and/or functional material 20. In this manner, certain components or functional elements of the chip 50 may be updated or modified without altering the geometry of the chip itself. For example, the insert assemblies 12 may be formed in a standard size. In the depicted embodiment, the recess 116 is formed in the microfluidic chip 50 by the middle passage 62 when the middle layer 54 is aligned with the bottom layer 52 (and bottom passage 60) or the top layer 56 (and the top passage 64). The recess 116 may be located anywhere, including on the interior or edges of the chip 50, and in any number on the microfluidic chip 50. The insert assembly 12 may be moved into the correct position by hand or utilizing robotic automation. After being positioned in the recess 116, the remaining layer (e.g., the top layer 56) may be aligned with the layers forming the recess 116.

In one embodiment, the insert assembly 12 may be undersized in at least one dimension to create one or more gaps or tolerances 118 within the recess 116. These tolerances 118 may be used to allow expansion or deformation of the insert assembly 12 during bonding and hence ensure proper sealing. In addition, the tolerances 118 facilitate pick-and-place assembly into the recess 116. Furthermore, in other embodiments, the insert assembly 12 may be slightly oversized relative to the recess 116 in other dimensions to facilitate expansion into the tolerances 118 under pressure. For example, the insert assembly 12 may deform under pressure (or other conditions) at an abutment surface 120 with the bottom layer 52 and/or an abutment surface 122 with the top layer 56.

The insert assembly 12 and the bottom layer 52, middle layer 54, and top layer 56 are coupled together at step 130. In one embodiment, the insert structure is formed from a material with thermal properties that are different to those of the material forming the chip layers. The different thermal properties may include different melting points and/or different temperatures of softening, yielding, or deformation of the materials. For example, under heat, either the insert assembly 12 or the recess 116 may be thermally reshaped to create a seal between the outer surface of the insert assembly 12 and the recess 116. In one example, the insert housing 14 is formed from a cyclic olefin co-polymer such as COC6015 with a melting point of about 150° C. and the chip layers are formed from the cyclic olefin co-polymer COC6017, which has a melting point of about 170° C. In such an embodiment, the insert housing 14 and the chip layers may be formed from different grades of the same material. That is, grades that differ in an amount of cross-linking of the polymer potentially in combination with additives, which in turn may influence the melting point. Further, the melting points may be selected for insert assembly 12 and chip 50 integrity during microfluidic processes (e.g., melting points above temperatures used during on-chip processes). The melting points may be far enough apart so that one of the structures deforms before the other. That is, if the chip layers have a lower melting point, exposure to the lower melting point only deforms the chip layers and not the insert assembly 14 and vice versa. In one embodiment, the melting points are at least 10° C. apart. The sealing between the insert assembly 14 and the chip layers may be encouraged by additional sealing structures, such as grooves or labyrinths, formed in the recess (e.g., in the cap 70, see FIG. 1) that material from insert housing 14 can fully or partially thermally yield into to form an enhanced or labyrinth bond or joint. Alternatively, the coupling may be accomplished via solvent bonding, radiation assisted bonding or other techniques. It should also be understood that certain embodiments of the disclosure may be implemented in which the substrate material deforms around an insert housing with a relatively higher deformation or melting temperature.

Figure 8:
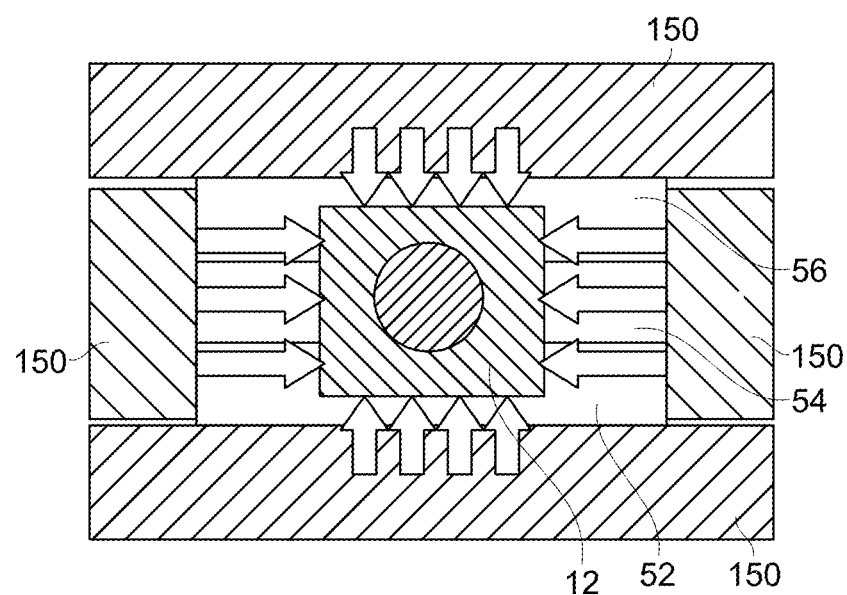
FIG. 8 is a cross-sectional view of a microfluidic chip assembly including a bonding frame in accordance with aspects of the present disclosure.

Additionally, the bonding can be assisted by a bonding frame around the chip layers during bonding (FIG. 8) which leads to an increase in bonding pressure from horizontal and vertical directions due to the thermal expansion of the chip and insert material. Alternatively, a hydrostatic press could be utilized for bonding. The strength of the bonding and sealing of the insert assembly 12 and the chip layers may be influenced by the tolerances chosen for the insert and/or the recess as well as the size of the insert housing 14.

EXAMPLES

Figure 9:
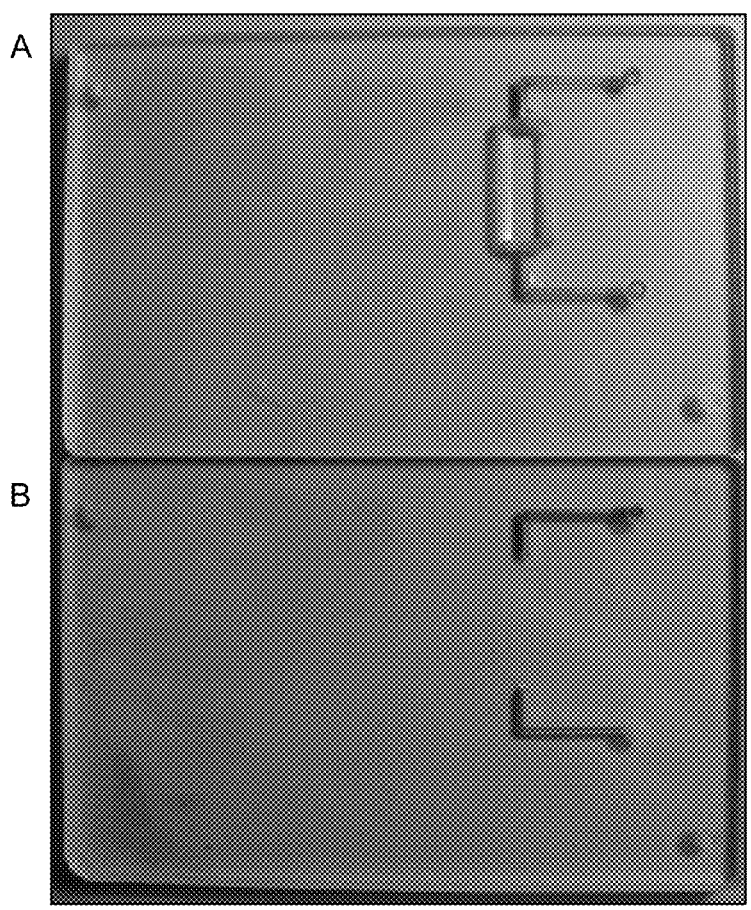
FIG. 9 is a top view of assembled and bonded chips comprising an insert in accordance with aspects of the present disclosure where the top chip A shows more delamination than the bottom chip B.
Figure 10:
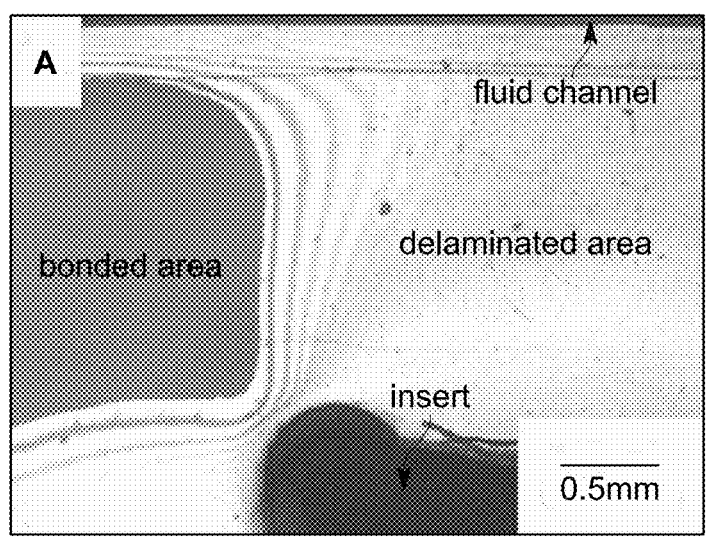
FIG. 10 shows a microscope image taken after chip manufacturing and bonding illustrating delamination areas in one chip assembly.
Figure 11:
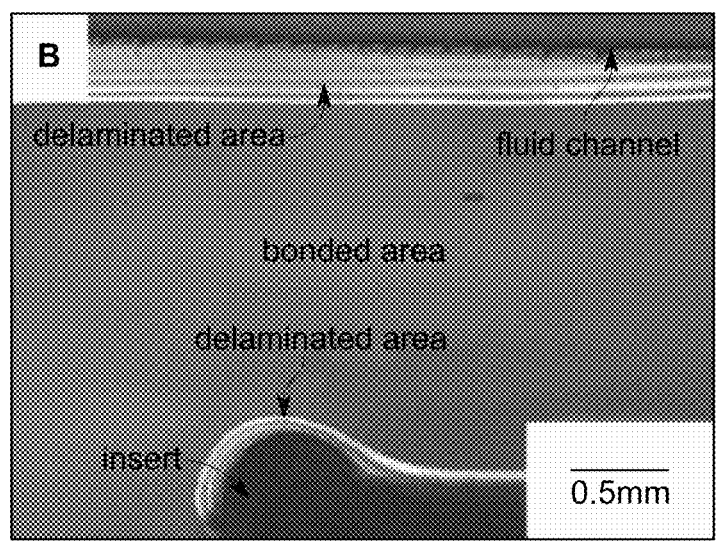
FIG. 11 shows a microscope image taken after chip manufacturing and bonding yielding reduced delamination areas in another chip assembly.

The concept has been tested with COC6015 and COC6017 inserts bonded between three layers of COC6017 (FIG. 9). The CO6015 insert thermally yielded into the recess structures, forming an even and optically transparent seal. Several bonding tests were executed to optimize bonding conditions and size of the COC6015 inserts. Too large inserts were associated with delamination between the layers as shown by microscope images taken after bonding (FIG. 10), which may lead to leakage into neighbor channels across the delaminated areas. This failure mode was recorded for a test chip during radiochemical evaluation (FIG. 11). There, radioactive 18-fluoride in an aqueous solution was leaking into neighbor channels and hence not recovered from the chip during operation, leading to an increase in residual on-chip activity measured. If the insert is too small, insufficient bonding takes place and leakage around the structure of interest may be the consequence.

Figure 12:
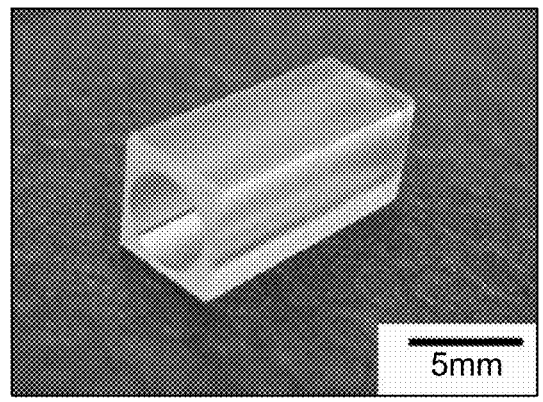
FIG. 12 is a perspective view of an insert component in accordance with aspects of the present disclosure.
Figure 13:
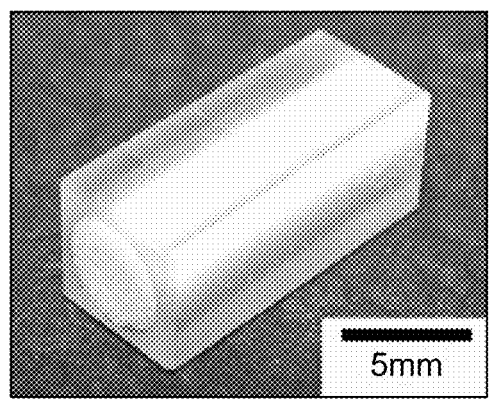
FIG. 13 is a perspective view of an insert assembly in accordance with aspects of the present disclosure.
Figure 14:
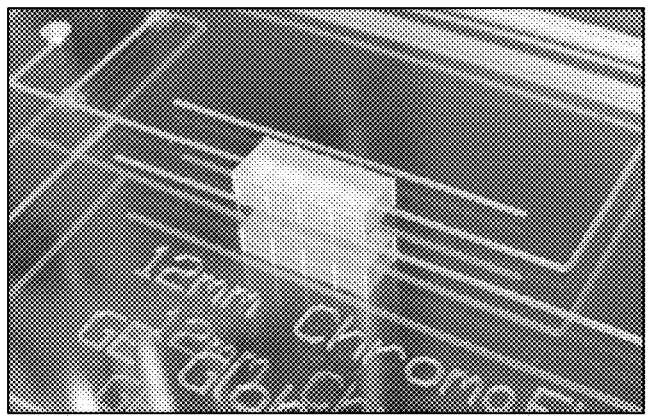
FIG. 14 is a perspective view of an assembled chip in accordance with aspects of the present disclosure.
Figure 15:
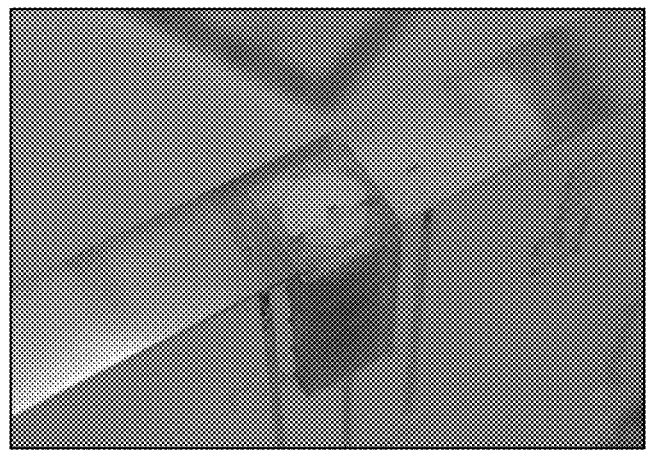
FIG. 15 is a cross-sectional view of the microfluidic chip of FIG. 14.

FIG. 12 is an empty insert housing, and FIG. 13 shows the insert housing filled with Chromabond (R) PS-HCO3 particles prior to bonding to the chip. Bonding was executed at 162° C., 90 min, 5 tons. The resulting on-chip Chromabond cartridges (see FIGS. 14 and 15 for perspective and cross-sectional views, respectively) were tested for trapping about 60-70 MBq of aqueous 18-fluoride (250 µl input). Subsequently, the trapped fluoride-18 was eluted utilizing 1 ml of Kryptofix K222 solution. The transfer efficiency for 18-fluoride trapping and release was measured to more than 90% and thus comparable to conventional state of the art methods in performance.

SPE/Solid resins play an important role in radiochemistry as well as other chemistries. For radiochemistry, on-chip ion exchange cartridges can build the interface between the cyclotron which delivers ~2 ml of radioactive solution, and a microfluidic synthesis system, which usually handles <500 µl volumes. This interface could consist of one optimized ion exchange cartridge or a combination of several cartridges that enable filtering of the cyclotron output from unwanted byproducts and impurities and concentration of the activity into small volumes <<500 µl. Furthermore, the on-chip integration of resins enables cryptate mediated F-18-fluorination using the potassium carbonate/kryptofix-system without azeotropic drying (Wessman et al., Nuklearmedizin (Vol. 51): Issue 1 2012 (1-31) to be executed on chip, thus mitigating any additional drying steps and evaporation. It is contemplated that the in-line insert assemblies 12 may be used to minimize radiation leakage and/or radiation waste on microfluidic chips 50 or radiation exposure to the operator by providing a contained and integrated solid phase extraction component within the insert assembly 12.

The technical effects of the present disclosure include providing a solid stationary phase that may be compatible and that may be used in conjunction with available microfluidic chip platforms and fluidic connectors, reactors and valves. That is, microfluidic chips incorporating insert assemblies may be used in conjunction with standard microfluidic platforms. Additional technical effects include relative low production costs (e.g. injection molding of standardized inserts and automated filling). Further, the microfluidic chips may be assembling with automated pick and place robotics devices. Because of the separate assembly and filling of the insert assemblies, changes or add-ons to the amount and type of resin may be adjusted without altering other chip assembly steps.

The present disclosure provides examples, including the best mode, and enables any person skilled in the art to practice the techniques disclosed herein, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A microfluidic chip comprising:
   a substrate with a microfluidic pathway and a passageway formed in the substrate that causes an in-line interruption of the microfluidic pathway, wherein the microfluidic pathway comprises a first terminus and a second terminus having the passageway disposed there between;
   an insert assembly in the passageway disposed in-line with the microfluidic pathway, wherein the insert assembly comprises a housing with a central bore and a functional material disposed in the bore, and wherein the insert assembly bridges the first terminus and the second terminus and the central bore is disposed in-line with the microfluidic pathway to complete the microfluidic pathway;
   a top layer disposed a first surface of the substrate; and
   a bottom layer disposed on a second surface of the substrate opposing the first surface, wherein at least one of the substrate, the top layer, or the bottom layer is formed from a first material comprising different thermal properties relative to a second material forming the insert housing of the insert assembly such that first material and the second material have different softening or melting temperatures.

2. The microfluidic device of claim 1, wherein the first material and the second material are different grades of cyclic olefin co-polymers.

3. The microfluidic device of claim 1, wherein melting points of the first material and the second material differ by at least 10 degrees Celsius.

4. The microfluidic device of claim 1, wherein the top layer comprises a cap or thinner covering portion that is bonded to the insert assembly.

5. The microfluidic device of claim 4, wherein the insert assembly comprises one or more mating features configured to mate with complementary features on an interior surface of the cap.

6. The microfluidic device of claim 1, further comprising one or more porous caps disposed on either end of the central bore and between the functional material and the microfluidic pathway.

* * * * *